United States Patent [19]

Wright, Jr. et al.

[11] Patent Number: 4,743,610

[45] Date of Patent: May 10, 1988

[54] N-[ω(3-PYRIDINYL)ALKYL]BENZAMIDES, USEFUL AS THROMBOXANE SYNTHETASE ENZYME AND/OR CARDIOPROTECTIVE AGENTS

[75] Inventors: William B. Wright, Jr., Woodcliff Lake; Andrew S. Tomcufcik, Old Tappan, both of N.J.

[73] Assignee: American Cyanamid Company, Stamford, Conn.

[21] Appl. No.: 26,224

[22] Filed: Mar. 16, 1987

[51] Int. Cl.[4] ..................... A61K 31/44; C07D 213/55
[52] U.S. Cl. .................................. 514/357; 546/335; 546/337
[58] Field of Search ................. 546/335, 337; 514/357

[56] References Cited

FOREIGN PATENT DOCUMENTS 0206662 12/1982 Japan ..................................... 546/337

*Primary Examiner*—Henry R. Jiles
*Assistant Examiner*—J. Richter
*Attorney, Agent, or Firm*—H. G. Jackson

[57] ABSTRACT

N-[ω(3-pyridinyl)alkyl]benzamides which are useful as inhibitors of thromboxane synthetase enzyme and/or as cardioprotective agents in the prevention of myocardial infarction.

17 Claims, No Drawings

N-[ω(3-PYRIDINYL)ALKYL]BENZAMIDES, USEFUL AS THROMBOXANE SYNTHETASE ENZYME AND/OR CARDIOPROTECTIVE AGENTS

BRIEF SUMMARY OF THE INVENTION

The invention is novel N-[ω-(3-pyridinyl)alkyl]benzamides represented by the structural formula:

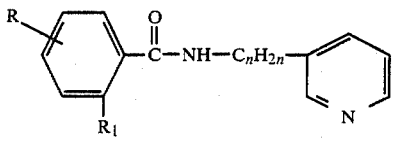

wherein n is an integer from 2-5, inclusive; R is hydrogen, alkyl having from one to four carbon atoms, halogen, alkyl having from one to four carbon atoms, halogen, trifluoromethyl, alkoxy having from one to four carbon atoms or nitro; $R_1$ is amino, alkylamino having from one to four carbon atoms or carboxy. The organic bases of this invention form non-toxic acid-addition salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, maleic, sulfamic, citric, lactic, malic, succinic, tartaric, acetic, benzoic, fumaric, gluconic, ascorbic, and the like.

The free bases of the invention are equivalent to their non-toxic acid-addition salts. The acid-addition salts of the organic bases of the present invention are, in general, relatively soluble in water, methanol and ethanol but relatively insoluble in nonpolar organic solvents such as diethyl ether, benzene, toluene, and the like.

DETAILED DESCRIPTION OF THE INVENTION

The invention is novel compounds of the formula:

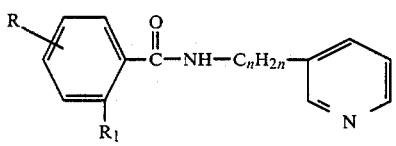

wherein n is an integer from 2-5 inclusive, R is hydrogen, alkyl having from one to four carbon atoms, halogen, trifluoromethyl, alkoxy having from one to four carbon atoms or nitro; $R_1$ is amino, alkylamino having from one to four carbon atoms or carboxy, or pharmaceutically acceptable salts thereof.

The novel compounds may be readily prepared as set forth in the following reaction schemes, wherein R, $R_1$, and n are as hereinabove defined:

Method 1

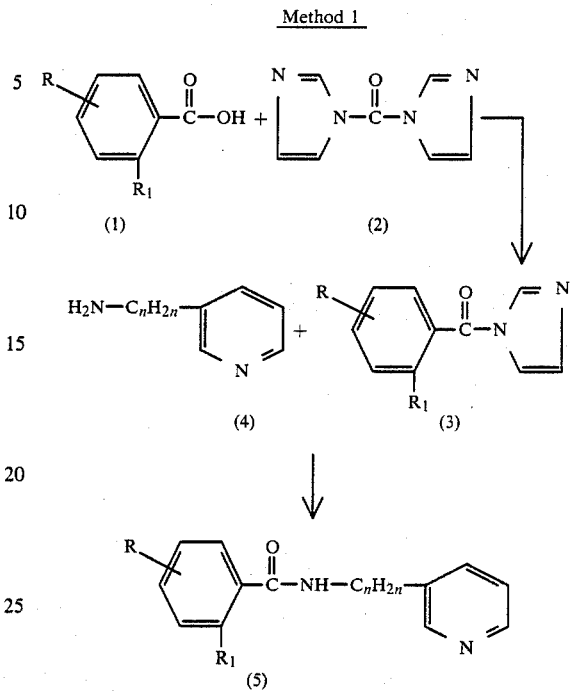

A benzoic acid derivative (1) is stirred in an inert solvent such as tetrahydrofuran and N,N'-carbonyldiimidazole (2) is added. The mixture is stirred for 1-24 hours at a temperature of about 0°-30° C. and the intermediate (3) is formed. The amine (4) is added and the mixture is allowed to react at 0°-60° for 1-24 hours and then concentrated. Water, dilute sodium hydroxide and an organic solvent such as methylene chloride are added and the desired product (5) is isolated by filtration or by concentration of the organic solvent.

Method II

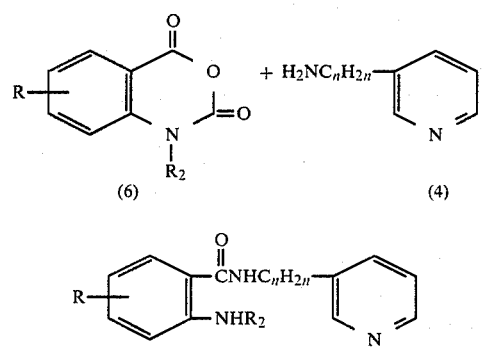

An appropriately substituted isatoic anhydride (6), wherein $R_2$ may be H or lower alkyl having from one to four carbon atoms, is reacted with a [ω-(3-pyridinyl)alkyl]amine (4) in an inert solvent such as dimethylsulfoxide, toluene or ethanol for 1-24 hours at ambient temperature or with heating at 60°-120° C. for 15-120 minutes. The product (7) is recovered from the reaction mixture.

Method III

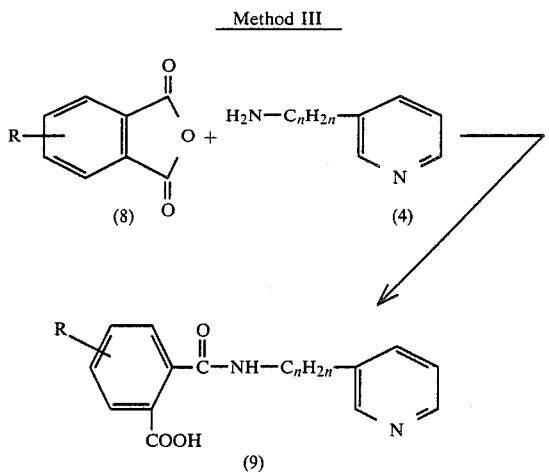

An appropriately substituted phthalic anhydride (8) is stirred in methylene chloride or a similar inert solvent and the amine (4) is added, preferably at 0°–30° C. The reaction mixture is allowed to stir at a preferred temperature of 20°–70° C. for 1–24 hours and the desired product (9) is recovered by filtration or concentration.

The amine intermediates (4) are described by J. M. Mayer and B. Testa, Helv. Chim. Acta. 65 (6) 1868 (1982).

The compounds of this invention inhibit thromboxane synthetase enzyme without interfering with other enzymes in the arachadonic acid cascade. Thus, these compounds are useful in the treatment of diseases characterized by an imbalance of thromboxane $A_2$/prostacyclin, such as ischemic heart disease, transient ischemic attack, thrombosis and migraine. Recent reviews have established the role of the thromboxane/prostacyclin balance in the vascular system [*Cardiovascular Diseases: New Trends in Surgical and Medical Aspects*, H. Barnett, P. Paoletti, E. Flamm and G. Brambilla, eds., Elsevier/North-Holland Biomedical Press, pp 137–150 (1981)]. Prostacyclin ($PGI_2$) is a potent vasodilator and platelet aggregation inhibitor, whereas thromboxane ($TXA_2$) is a powerful vasoconstrictor and inducer of platelet aggregation. $TXA_2$ synthesis is catalyzed by thromboxane synthetase enzyme located in, for example, blood platelets. When $TXA_2$ production is increased relative to $PGI_2$, platelet aggregation, thrombosis and vasospasm may occur [Lancet, 1, 479 (1977): Lancet, 1 1216 (1977); Science, 1931, 1135 (1976); Amer. J. Cardiology, 41 787 (1978)]. $TXA_2$ synthetase inhibitors have been shown to have anti-thrombotic action superior to that of aspirin [*J. Clin. Invest.*, 65, 400 (1980); Br. J. Pharmac., 76, 31982].

The role of prostaglandins including $TXA_2$ and $PGI_2$ in ischemic heart patients has been reviewed [*Cardiovascular Pharmacology of the Prostaglandins*, A. G. Herman, P. M. Vanhoute, H. Denolin and G. Goosens, eds., Raven Press, New York, pp 361–374 (1982)], Injection of $TXA_2$ into coronary arteries of guinea pigs and rabbits causes myocardial ischemia and subendocardial necrossis [*Drugs of Furture*, 7, No. 5 331, (1982); Proc. Jap. Acad., 53(B), 38 (1977); Eur. J. Pharmacol., 53 49 (1978)]. Recent research has demonstrated the beneficial effects of $PGI_2$ and selective inhibition of thromboxane synthetase on ischemic myocardium in canines [*J. Cardiovascular Pharmacology*, 4, 129 (1982)]. Thus compounds which selectively inhibit thromboxane synthetase (and hence $TXA_2$) without adversely affecting $PGI_2$ are useful in the treatment of vascular diseases such as ischemia and migraine. In addition, inhibition of $TXA_2$ formation may effectively treat platelet aggregation and prevent thrombosis.

Under urethan anesthesia, 10 µl of arterial blood was collected in one ml. of 3.2% sodium citrate in a polystyrene tube from Okamoto-Aoki spontaneously hypertensive rats (SHR) (Taconic Farms, Germantown, N.Y.) between 19 and 24 weeks in age. The blood was diluted with 3 ml. of cold saline and centrifuged at room temperature for 15 minutes at 460×g. The platelet rich plasma (PRP) was separated. The platelets were isolated by centrifuging the PRP for 10 minutes at 1060 xg and were washed in 4 ml. of cold oxygenated Krebs phosphate buffer, pH 7.4. The chilled platelets recovered from centrifuging at 800×g for 10 minutes were resuspended in oxygenated Krebs phosphate buffer and diluted to contain $4.5-6.0\times10^4$ platelets/µl.

The inhibition of thromboxane (TX) formation was studied by determining the concentration of thromboxane $B_2$ ($TXB_2$), the stable hydrolysis product of $TXA_2$. Assay samples, prepared on ice, contained 200 µl platelet suspension, 50 µl saline, and 50 µl vehicle or drug under study (OKY1581, UK-37248-01, 1-benzylimidazole, or indomethacin). The samples were incubated for 10 minutes at 37° C. in a metabolic shaker. The reaction was terminated by immersing the tubes in an ice bath and adding 50 µl of 0.5M citric acid. The samples were centrifuged for 10 minutes in a refrigerated centrifuge and the supernatants thus obtained were decanted and stored at −20° C. The $TXB_2$ content for each sample was determined by a direct radioimmunoassay (RIA) utilizing a $TXB_2$ specific RIA kit purchased from New England Nuclear, Boston, MA. and expressed as pg $TXB_2$ formed minute$^{-1}$ sample$^{-1}$, from which the percent inhibition of $TXB_2$ formation was calculated. The results of this test on representative compounds of this invention appear in Table I below.

TABLE I

| Compound | % Inhibition |
|---|---|
| 2-Amino-5-chloro-N—[3-(3-pyridinyl)propyl]benzamide dihydrochloride | 98 |
| 2-Amino-4-chloro-N—[3-(3-pyridinyl)propyl]benzamide | 95 |
| 2-Amino-N—[3-(3-pyridinyl)propyl]-3-(trifluoromethyl)benzamide dihydrochloride | 98 |
| 2-Amino-N—[4-(3-pyridinyl)butyl]benzamide dihydrochloride | 97 |
| 2-Amino-4-chloro-N—[4-(3-pyridinyl)butyl]benzamide dihydrochloride | 99 |
| 2-Amino-4-chloro-N—[4-(3-pyridinyl)butyl]benzamide dihydrochloride | 98 |
| 2-Amino-5-methyl-N—[4-(3-pyridinyl)butyl]benzamide dihydrochloride | 100 |
| 5-Chloro-2-(methylamino)-N—[4-(3-pyridinyl)butyl]benzamide dihydrochloride | 99 |
| 4-Chloro-2-[[[4-(3-pyridinyl)butyl]amino]carbonyl]benzoic acid | 100 |
| 2-[[[4-(3-pyridinyl)butyl]amino]carbonyl]benzoic acid | 92 |

The novel compounds of the present invention are also active as cardioprotective agents. Fibrillation, arrhythmia and irreversible infarction are all integrally related to the lack of oxygen supply to the heart muscle. A drug which can prevent serious damage to the heart in situations of abnormally low oxygen supply may allow the patient to survive an infarction.

An in vivo test which demonstrates the prevention of death due to infarction described by D. L. Crandall, D. R. Griffith and D. C. Beitz, *Toxicology and Applied Pharmacology* 62, 152–157 (1982) was performed as follows:

In Vivo Test for the Prevention of Death Due to Infarction

Sprague-Dawley rats were pretreated with an intraperitoneal injection of the test compound at 10 mg/kg of body weight. One hour later, a myocardial infarction was induced by injection 10 mg/kg of (-)isoproternol hydrochloride subcutaneously. Each compound was tested in at least three rats. The animals were observed for 2.5 hours. The compound is considered "in vivo active" in those groups in which all animals survive the myocardial infarction. The results of this test appear in Table II.

TABLE II

In Vivo Results for the Prevention of Death Due to Infarction

| Compound | No. of Rats Infarcted | No. of Rats Surviving | % Survival |
|---|---|---|---|
| 2-Amino-N—[2-(3-pyridinyl)ethyl]benzamide | 3 | 3 | 100 |
| 2-Amino-4-chloro-N—[3-(3-pyridinyl)propyl]benzamide, dihydrochloride | 3 | 3 | 100 |
| 2-Amino-N—[4-(3-pyridinyl)butyl]benzamide, dihydrochloride | 3 | 3 | 100 |
| 2-Amino-4-chloro-N—[4-(3-pyridinyl)butyl]benzamide, dihydrochloride | 3 | 3 | 100 |
| 2-Amino-5-chloro-N—[4-(3-pyridinyl)butyl]benzamide, dihydrochloride | 3 | 3 | 100 |
| 2-Amino-5-methyl-N—[4-(3-pyridinyl)butyl]benzamide, dihydrochloride | 3 | 3 | 100 |
| 4-Chloro-2-[[[4-(3-pyridinyl)butyl]amino]carbonyl]benzoic acid | 3 | 3 | 100 |
| 2-[[[2-(3-Pyridinyl)ethyl]amino]carbonyl]benzoic acid | 3 | 3 | 100 |

The novel compounds of the present invention have been found to be highly useful for inhibiting thromboxane synthetase and acting as cardioprotective agents in mammals when administered in amounts ranging from about 0.1 mg to about 20.0 mg/kg of body weight per day. A preferred dosage regimen for optimum results would be from about 0.5 mg to about 10.0 mg/kg of body weight per day. Such dosage units are employed that a total of from about 35 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a carrier vehicle of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have a molecular weight of from about 200 to 1500. Although the amount of active compound dissolved in the above vehicle may vary from 0.10% to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristylgamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard to soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% and about 60% of the weight of the unit. The amount of active compound in such therapeutically useful compositions is such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccarin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propyl parabens as preservatives, a dye and flavoring such as cherry or orange flavor. Of course, any material used in preparing any dosage unit form should be pharmaceutically pure and substantially non-toxic in the amounts employed.

The following specific examples illustrate the preparation of the compounds of the present invention.

EXAMPLE 1

2-Amino-N-[2-(3-pyridinyl)ethyl]benzamide

A mixture of 4.89 g of isatoic anhydride, 3.66 g of 2-(3-pyridinyl)ethylamine and 40 ml of ethanol was stirred at room temperature for 22 hours. The reaction mixture was concentrated and the residue was dissolved in ethyl acetate and cooled. The desired product was isolated by filtration, mp 126°–128° C.

EXAMPLE 2

2-Amino-N-[4-(3-pyridinyl)butyl]benzamide dihydrochloride

A mixture of 3.25 g of isatoic anhydride, 3.0 g of 4-(3-pyridinyl)butylamine and 20 ml of dimethylsulfoxide was allowed to stand overnight at room temperature, then was treated with 40 ml of water, 10 ml of 1N sodium hydroxide and 200 ml of methylene chloride. The organic layer was separated, washed with water, dried over magnesium sulfate and concentrated. The oily residue was mixed with ethanolic hydrogen chloride and concentrated. The residue was triturated with ether to obtain the desired product, mp 220°–223° C.

EXAMPLE 3

2-Amino-5-chloro-N-[4-(3-pyridinyl)butyl]benzamide dihydrochloride

The above compound, mp 200° C., was obtained when 5-chloro-isatoic anhydride was substituted for isatoic anhydride in the procedure of Example 2.

EXAMPLE 4

5-Chloro-2-(methylamino)-N-[4-(3-pyridinyl)butyl]benzamide dihydrochloride

When 5-chloro-N-methyl isatoic anhydride was substituted for isatoic anhydride in the procedure of Example 2, the above compound, mp 161°–163° C., was obtained.

EXAMPLE 5

2-Amino-5-nitro-N-[4-(3-pyridinyl)butyl]benzamide dihydrochloride

When 5-nitro isatoic anhydride is treated with 4-(3-pyridinyl)butylamine by the procedure of Example 2, the above compound is obtained.

EXAMPLE 6

2-Amino-4-Chloro-N-[4-(3-pyridinyl)butyl]benzamide dihydrochloride

A mixture of 1.72 g of 4-chloroanthranilic acid, 1.62 g of N,N'-carbonyldiimidazole and 25 ml of tetrahydrofuran was stirred for 3 hours at 5°–25° C. and 1.50 g of 4-(3-pyridinyl)butylamine was added. The mixture was stirred overnight at room temperature, heated at reflux temperature for 1 hour and then with 10 ml of water for 30 minutes. The reaction mixture was concentrated and 100 ml of methylene chloride and 5 ml of 1N sodium hydroxide were added. The layers were separated and the organic layer was concentrated, washed with water, dried over magnesium sulfate and concentrated. The residue was treated with ethanolic hydrogen chloride. The mixture was again concentrated and triturated with acetone to obtain crystals of the desired product, mp 208°–210° C. after recrystallization from ethanol.

EXAMPLE 7

2-Amino-5-methyl-N-[4-(3-pyridinyl)butyl]benzamide dihydrochloride

The above compound, mp 184°–186° C., was obtained when 5-methylanthranilic acid was reacted with 4-(3-pyridinyl)butylamine by the procedure of Example 6.

EXAMPLE 8

2-Amino-5-methoxy-N-[4-(3-pyridinyl)butyl]benzamide dihydrochloride

When 5-methoxyanthranilic acid is reacted with 4-(3-pyridinyl)butylamine by the procedure of Example 6, the above compound is obtained.

EXAMPLE 9

2-Amino-4-chloro-N-[3-(3-pyridinyl)propyl]benzamide

A mixture of 3.43 g of 4-chloroanthranilic acid, 3.24 g of N,N'-carbonyldiimidazole and 50 ml of tetrahydrofuran was stirred at 5°–25° C. for 3 hours and 4.18 g of 3-(3-pyridinyl)propylamine dihydrochloride was added. The reaction mixture was stirred at room temperature for 18 hours, heated at reflux temperature for one hour and then with 10 ml of water for 30 minutes. The mixture was concentrated and treated with 100 ml. of methylene chloride and 10 ml of 1N sodium hydroxide. The layers were separated and the organic layer was washed with water, dried over magnesium sulfate and concentrated. The residue was recrystallized from ethyl acetate and the desired product, mp 145°–147° C. was obtained.

EXAMPLE 10

2-Amino-5-chloro-N-[3-(3-pyridinyl)propyl]benzamide

The above product, mp 129°–130° C. was obtained when 5-chloroanthranilic acid was substituted for 4-chloroanthranilic acid in the procedure of Example 9. The dihydrochloride salt prepared as described in Example 6 melts at 217°–219° C.

EXAMPLE 11

2-Amino-N-[3-(3-pyridinyl)propyl]-3-(trifluoromethyl)-benzamide dihydrochloride

The above compound was obtained when 3-trifluoromethyl anthranilic acid was reacted with 3-(3-pyridinyl)propylamine dihydrochloride by the procedure of Example 9, the dihydrochloride salt prepared as described in the procedure of Example 6 melts at 149°–150° C.

EXAMPLE 12

2-[[[2-(3-Pyridinyl)ethyl]amino]carbonyl]benzoic acid

A mixture of 4.44 g of phthalic anhydride and 75 ml of methylene chloride was stirred and 3.66 g of 2-(3-pyridinyl)ethylamine was added. Solution occured followed by separation of a white precipitate. The desired product was separated by filtration and melted at 183°–185° C.

EXAMPLE 13

2-[[[4-(3-Pyridinyl]butyl]amino]carbonyl]benzoic acid

When 4-(3-pyridinyl)butylamine was substituted for 2-(3-pyridinyl)ethylamine in the procedure of Example 12, the above compound, mp 132°–135° C. was obtained.

EXAMPLE 14

4-Chloro-2-[[[4-(3-pyridinyl)butyl]amino]carbonyl]benzoic acid

When 5-chlorophthalic anhydride was reacted with 4-(3-pyridinyl)butylamine by the procedure of Example 12, the above compound, mp 152°–154° C. was obtained.

EXAMPLE 15

2-Amino-N-[5-(3-pyridinyl)pentyl]benzamine dihydrochloride

When isatoic acid is treated with 5-(3-pyridinyl)pentylamine by the procedure of Example 2, the above compound is obtained.

We claim:

1. A compound of the formula:

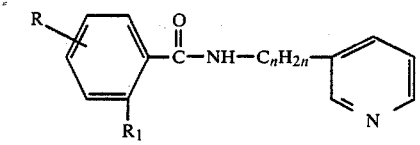

wherein n is an integer from 2–5 inclusive, R is hydrogen, alkyl having from one to four carbon atoms, halogen, trifluoromethyl, alkoxy having from one to four carbon atoms or nitro; $R_1$ is amino, alkylamino having from one to four carbon atoms or carboxy, or pharmaceutically acceptable salts thereof.

2. A compound according to claim 1, 2-amino-N-[2-(3-pyridinyl)ethyl]benzamide.

3. A compound according to claim 1, 2-amino-N-[4-(3-pyridinyl)butyl]benzamide dihydrochloride.

4. A compound according to claim 1, 2-amino-5-chloro-N-[4-(pyridinyl)butyl]benzamide dihydrochloride.

5. A compound according to claim 1, 5-chloro-2-(methylamino)-N-[4-(3-pyridinyl)butyl]benzamide dihydrochloride.

6. A compound according to claim 1, 2-amino-4-chloro-N-[4-3-(pyridinyl)butyl]benzamide dihydrochloride.

7. A compound according to claim 1, 2-amino-5-methyl-N-[4-(3-pyridinyl)butyl]benzamide dihydrochloride.

8. A compound according to claim 1, 2-amino-4-chloro-N-[3-(3-pyridinyl)propyl]benzamide.

9. A compound according to claim 1, 2-amino-5-chloro-N-[3-(3-pyridinyl)propyl]benzamide dihydrochloride.

10. A compound according to claim 1, 2-amino-N-[3-(3-pyridinyl)propyl]-3-(trifluoromethyl)benzamide dihydrochloride.

11. A compound according to claim 1, 2-[[[2-(3-pyridinyl)ethyl]amino]carbonyl]benzoic acid.

12. A compound according to claim 1, 1-[[[4-(3-pyridinyl)butyl]amino]carbonyl]benzoic acid.

13. A compound according to claim 1, 4-chloro-2-[[[4-(3-pyridinyl)butyl]amino]carbonyl]benzoic acid.

14. A method of inhibiting thromboxane synthetase enzyme in a mammal which comprises administering internally to the mammal a thromboxane synthetase inhibiting amount of a compound of the formula:

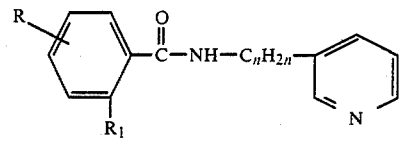

wherein n is an integer from 2–5 inclusive; R is hydrogen, trifluoromethyl, alkoxy having from one to four carbon atoms or nitro; $R_1$ is amino, alkylamino having from one to four carbon atoms or carboxy or pharmaceutically acceptable salts thereof.

15. A method for preventing myocardial infarction in a mammal which comprises administering internally to the mammal a myocardial infarction inhibiting amount of a compound of the formula:

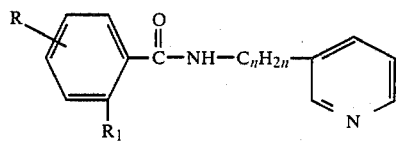

wherein n is an integer from 2–5 inclusive; R is hydrogen, alkyl having from one to four carbon atoms, halogen, trifluoromethyl, alkoxy having from one to four carbon atoms or nitro; $R_1$ is amino, alkylamino having from one to four carbon atoms or carboxy or pharmaceutically acceptable salts thereof.

16. A thromboxane sythetase enzyme inhibiting composition of matter in dosage unit form comprising from about 10 mg to about 700 mg of a compound of the formula:

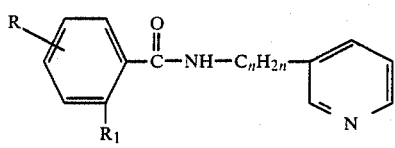

wherein n is an integer from 2–5 inclusive; R is hydrogen, alkyl having from one to four carbon atoms, halogen, trifluoromethyl, alkoxy having from one to four carbon atoms or nitro; $R_1$ is amino, alkylamino having from one to four carbon atoms or carboxy or pharmaceutically acceptable salts thereof and a pharmaceutically acceptable carrier.

17. A composition of matter in dosage unit form for the prevention of myocardial infarction comprising from about 10 mg to about 700 mg of a compound of the formula:

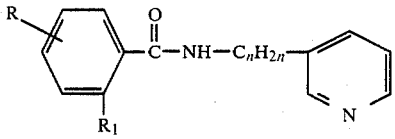

wherein n is an integer from 2–5 inclusive, R is hydrogen, alkyl having from one to four carbon atoms, halogen, trifluoromethyl, alkoxy having from one to four carbon atoms or nitro; $R_1$ is amino, alkylamino having from one to four carbon atoms or carboxy or pharmaceutically acceptable salts thereof and a pharmaceutically acceptable carrier.

* * * * *